(12) United States Patent
Fan et al.

(10) Patent No.: US 7,730,775 B2
(45) Date of Patent: Jun. 8, 2010

(54) CHARACTERIZATION OF LIQUID, WATER AND/OR MOISTURE TRANSPORT PROPERTIES OF FABRICS

(75) Inventors: Jintu Fan, Hong Kong SAR (CN); Xiaoming Qian, Hong Kong SAR (CN)

(73) Assignee: The Hong Kong Polytechnic University, Hong Kong SAR (CN)

( * ) Notice: Subject to any disclaimer, the term of this patent is extended or adjusted under 35 U.S.C. 154(b) by 645 days.

(21) Appl. No.: 11/634,077

(22) Filed: Dec. 6, 2006

(65) Prior Publication Data

US 2008/0134769 A1 Jun. 12, 2008

(51) Int. Cl.
*G01L 5/04* (2006.01)
(52) U.S. Cl. ........................................... 73/159
(58) Field of Classification Search ............... 73/159
See application file for complete search history.

(56) References Cited

U.S. PATENT DOCUMENTS

| | | | | |
|---|---|---|---|---|
| 3,881,489 A | * | 5/1975 | Hartwell | 604/369 |
| 4,868,967 A | * | 9/1989 | Holt et al. | 29/450 |
| 5,070,597 A | * | 12/1991 | Holt et al. | 29/887 |
| 5,454,800 A | * | 10/1995 | Hirt et al. | 604/378 |
| 5,599,335 A | * | 2/1997 | Goldman et al. | 604/368 |
| 5,887,477 A | * | 3/1999 | Newman | 73/159 |
| 6,187,696 B1 | * | 2/2001 | Lim et al. | 442/77 |
| 6,595,042 B2 | * | 7/2003 | Holliday et al. | 73/64.47 |
| 6,664,439 B1 | * | 12/2003 | Arndt et al. | 604/378 |
| 7,169,720 B2 | * | 1/2007 | Etchells et al. | 442/239 |
| 2007/0017291 A1 | * | 1/2007 | Cypes et al. | 73/590 |

* cited by examiner

*Primary Examiner*—Hezron Williams
*Assistant Examiner*—Rodney T Frank
(74) *Attorney, Agent, or Firm*—Buchanan Ingersoll & Rooney PC

(57) ABSTRACT

A transplanar liquid transport tester for fabrics, comprising a liquid reservoir; a liquid-permeable support member having a first surface for supporting a fabric test sample, and a second surface for interfacing with liquid in the liquid reservoir; and means for maintaining a constant hydrostatic pressure in the liquid reservoir at the second surface of the support member for replenishing liquid through the support member to the first surface during testing.

26 Claims, 4 Drawing Sheets

CHARACTERIZATION OF LIQUID, WATER AND/OR MOISTURE TRANSPORT PROPERTIES OF FABRICS

FIELD OF THE INVENTION

The present invention relates to characterization of fabric properties, and more particularly, to characterization of the liquid, water and/or moisture transport properties of a fabric. More specifically, the invention relates to real-time measurement of water loss in water or moisture transport tests.

BACKGROUND OF THE INVENTION

The transmission of water or moisture through fabric or clothing assemblies is an important property—significant to the thermal comfort of clothing.

There are numerous standard test methods for determining both moisture transmission and liquid water transport through fabrics or clothing. The most commonly used methods for evaluating the moisture transmission rate or moisture vapour resistance through fabrics or clothing assemblies are the upright cup method (ASTM E96-80-Procedure B) and the Sweating Hotplate Method (ISO 11092). The former determines the water loss from a dish covered with a fabric sample over a specific period of time. Test results are normally reported in g/m$^2$/24 hrs. The latter method determines evaporative heat loss over a gradient of water vapour pressure and reports the results as water vapour resistance in m$^2$ Pa/W.

There are four general test method types for measuring the wicking or water transport properties through fabrics—namely: longitudinal wicking "strip" tests; transverse (or Transplanar) wicking "plate" tests; aerial wicking "spot" tests; and Syphon tests [1].

Two longitudinal wicking "strip" tests are established as industrial standards—namely: BS3424 Method 21 (1973)—Determination of Resistance to Wicking; and DIN 53924 (1978)—Determination of the Rate of Absorption of Water by Textile Materials (Height of Rise Method). Both of these methods use a preconditioned strip of test fabric suspended vertically with its lower end immersed in a reservoir of distilled water to which a die of a type known not to affect the wicking behaviour may be added for visually tracking the movement of the water. After a fixed period of time, the height reached by the water in the fabric above the water level in the reservoir is measured. The BS3424 Method 21 specifies a very long time period (24 hours) and is intended for coated fabrics with very slow wicking, whereas DIN 53924 specifies a much shorter time for the test (5 minutes maximum) and is appropriate for relatively rapid-wicking fabrics. Since water transport in clothing is generally transplanar (across the fabric plane), the measurement of a fabric's wickability in the fabric plane as measured by longitudinal wicking "strip" tests has limited implications to the measurement of clothing comfort.

Insofar as transverse (or transplanar) wicking "plate" tests are concerned, no published standards exist to date. An apparatus for this test was first implemented by Barus et al [2] and consisted of a horizontal sintered glass plate fed from below with water from a horizontal capillary tube, the level of which is set so that the upper surface of the plate is kept damp, as a simulation of a sweating skin surface. A disc of test fabric is placed on the plate and held in contact therewith under a defined pressure applied by placing weights upon it. The position of the meniscus along the capillary tube is recorded at various time intervals as water is wicked through the fabric layer. Given the diameter of the capillary tube, the recorded position of the meniscus can be used to calculate the mass transfer rate of water into the fabric. A disadvantage of this method is that the resistance to flow imposed by the capillary tube decreases and the hydrostatic head decreases during the course of the test as water wicks up through the fabric sample.

Hussain and Tremblay-Lutter [3] also described a test for measuring the transplanar uptake of liquids by fibrous materials is in contact with a liquid. An instrument adopting a DAMT (Dynamic Absorbency Measurement Technique) had a liquid reservoir which continuously supplied liquid to sample cells via pipes. The changing weight of the reservoir was measured by an electronic balance to measure the rate of liquid uptake by the textile material in the sample. A disadvantage in this technique is that the control of the liquid level is dependent on the sensitivity and accuracy of the elastic properties of the mechanical spring which is supporting the liquid reservoir.

There are two published aerial wicking "spot" test standards of measurement, namely: BS3554 (1970), Determination of Wettability of Textile Fabrics; and AATCC Method 39-1977—Evaluation of Wettability. In these standard tests, a drop of liquid (either distilled water, or for highly wettable fabrics—a 50% sugar solution) is delivered from a height of approximately 6 millimetres onto a horizontal fabric test specimen. The elapsed time between the drop reaching the fabric surface and the disappearance of a reflection from the liquid surface is taken as a measure of how quickly the liquid has spread over and wetted the fabric surface. The disadvantage of this method is that the supply water is not continuous as is the case during sweating.

Another aerial wicking "spot" test method is known as Moisture Management of Textiles (MMT) [4]. Moisture management indexes are determined by MMT for a textile sandwiched between two electrically conductive plates by measuring changes in electrical resistance across the plates. These measurements indicate changes in water content. A quantity of liquid is poured upon the upper surface of the fabric. The liquid is then transported three-dimensionally through the fabric. Based on the measurement of electrical resistance between the upper and lower plates via the surfaces of the fabric, moisture management indexes (which included accumulated liquid absorption of the upper and lower surfaces of the fabric; maximum difference between the water content of the upper and lower surfaces; and initial absorption speeds and drying rates at the upper and lower surfaces) can be calculated.

Tanner [2] and Lennox-Kerr [5] report syphon tests. A rectangular strip of test fabric is used as a syphon with one end immersed in a reservoir of water or saline solution and the other end placed at a lower level in a collection beaker. The amount of liquid transferred during successive time intervals can be determined by weighing the collection beaker. This is a simple test, but does not simulate the transport of liquid through clothing during sweating.

In each of the methods described above, there are two fundamental disadvantages. Firstly, the water level in a reservoir (cup, beaker, or tube etc) reduces as water vapour is transmitted through the fabric or as liquid water is absorbed and transported through the fabric. The reduction in water level results in an increase in the air-exposed surface area of the sample and a change in water pressure between the fabric and the water surface, which results in inconsistent test results. Secondly, in many of the tests described, it is not possible to measure water loss (transmitted in vapour form or transported in the form of water) continuously in real-time.

REFERENCES

1. Harnett, P. R. and Mehta, P. N., A Survey and Comparison of Laboratory Test Methods for Measuring Wicking, Textile Research Journal, July 1984.
2. Buras, E. M., Goldthwaite, C. F., and Kraemer. R. M., Measurement and Theory of Absorbency of Cotton Fabrics, Tex. Res. J. 20, 239-248 (1950)
3. Hussain, M. M. and Tremblay-Lutter, J. F., A Test Method for Measuring Liquid Penetration through Fibrous Materials, Performance of Protective Clothing: Fifth Volume, ASTM STP 1237, James S. Johnson and S. Z. Mansdorf, Eds., American Society for Testing and Materials, 1996.
4. U.S. Pat. No. 6,499,338 entitled: Moisture Management of Textiles Yi Li, Weilin Xu, Kwok-wing Yeung and Yi-Lin Kwok.
5. Lennox-Kerr, P., Leaglor: Super-Absorbent Acrylic from Italy, Textile Inst. Ind. 19, 83-84 (1981).

OBJECT OF THE INVENTION

It is an object of the present invention to overcome or substantially ameliorate at least one of the above disadvantages and/or more generally to provide an improved real-time water or moisture transport test apparatus and method for fabrics in which constant water level/hydrostatic pressure adjacent to the test sample is maintained.

SUMMARY OF THE INVENTION

According to the present invention, there is provided a method of characterising the liquid water or moisture transmission properties of a fabric, the method comprising the steps of filling a container with a test liquid, delivering said test liquid from said container towards said fabric for transmission of said test liquid from the apparatus to external of the apparatus through said fabric, supplying said test liquid from a source reservoir to said container to replenish liquid lost from said container due to transmission of moisture through said fabric, and measuring the amount of liquid loss from said source reservoir to determine the moisture transmission characteristics of said fabric.

By using this method, the liquid, water or moisture transport properties of a fabric can be evaluated by monitoring the loss of liquid from the reservoir. This arrangement facilitates the possibility of separately locating the source reservoir and the testing container so that the fabric can be tested under various indoor or outdoor conditions while the source reservoir and data collection devices could be kept in a controlled or secured environment. More importantly, by employing a source reservoir and a testing container separately, and by monitoring the amount of test liquid loss at the testing container through the fabric by monitoring the amount of test liquid replenished by the source reservoir, more accurate measurements of fabric liquid, water or moisture transport properties can be obtained. Moreover, by separating the source reservoir and the testing container at which the characterising tests are actually done, many different forms and configuration of the test containers can be designed to fulfil different modes of characterisation.

To mitigate inaccuracy due to evaporation of test liquid from the source reservoir, the container defines an aperture through which the test liquid contained in said container is transmissible outside of said container, and the method comprises covering said aperture with a fabric to be characterised.

The liquid level in the source reservoir may be maintained to be the same as the liquid level in the said container by hydrostatic pressure.

In order to accurately monitor the loss of test liquid from the test container, the volume of test liquid in said container may be maintained constant by the replenishing liquid during the fabric characterisation process.

Similarly, the level of test liquid in the container relative to said fabric may be maintained constant during the fabric characterisation process, so that the source reservoir only needs to replenish the test container with the test liquid to the constant level.

As an alternative, the hydrostatic pressure of the test liquid in said container relative to said fabric may be monitored to ensure that the hydrostatic pressure remains constant during the fabric characterisation process.

To enhance accuracy, the volume of test liquid contained in said source reservoir may be smaller than the volume of test liquid in said container. By monitoring the loss of test liquid from a reservoir of a smaller volume, a higher data accuracy can be obtained.

As an example, the volume of test liquid contained in said source reservoir may be smaller than 50% of the volume of test liquid in said container.

As a further example, the fabric and the test liquid in said container may be arranged to simulate sweating conditions of a human being.

To simply the data evaluation procedures, the fabric and the container may be arranged so that loss of liquid from said container is solely due to transmission through said fabric.

In a preferred embodiment, the fabric forms at least part of said container and defining said aperture.

To adapt for evaluating fabric properties corresponding to various postures of a human being, during, for example, different activity modes, the shape of the container defined by said fabric may be reconfigurable to simulate a plurality of postures of a human being.

According to a second aspect of this invention, there is provided a fabric characterization apparatus for characterising the liquid, water or moisture transmission properties of a fabric, the apparatus comprising a container for receiving a test liquid and for supplying said test liquid to a fabric of which the moisture transmission properties are to be characterised, a source reservoir for supplying said test liquid to said container for replenishing said container with said test liquid to compensate for loss of said test liquid from said container, and a monitoring device for recording and monitoring the supply of the replenishing liquid from said source reservoir to said container.

To deliver the test fluid to a fabric which may be located away from the container, the apparatus may comprise an arrangement for delivering the test liquid from said container to the fabric. For example, the apparatus may comprise a receptacle for receiving said fabric, said receptacle defining an aperture through which said test liquid is transmissible outside of said container through said fabric.

To evaluate the data collected by the monitoring device, the apparatus further comprising a processor for compiling data taken by said monitoring device to evaluate liquid, water or moisture transport properties of a fabric to be characterised.

In an embodiment, the test container comprises a receptacle defining said apertures and for receiving a fabric to be characterised, said receptacle and said aperture may be arranged such that loss of test liquid from said container being solely through said aperture and said fabric.

For easy management of the test container, the level of said receptacle relative to said test liquid in said container may be adjustable.

In a preferred embodiment, the container may comprise a liquid-permeable support member having a first surface for supporting a fabric test sample, and a second surface for interfacing with the test liquid in the source reservoir For simpler monitoring, the container may comprise an overflow arrangement for maintaining a constant level or a constant volume of test liquid in said container, and said monitoring device is also arranged to monitor the overflow of said test liquid.

To cater for different testing conditions and objectives, the overflow level of said overflow arrangement may be adjustable.

As an example, an overflow return arrangement may be provided for returning the overflowed test liquid to said source reservoir.

To cater for yet other different testing conditions and objectives, the container may be reconfigurable for simulating a plurality of postures of a human being.

In an example, the test liquid in said container may be substantially surrounded by the fabric under characterisation. Such an arrangement would ensure a large testing surface for enhanced data collection or for collecting daa according to different requirements.

As a further example, the test container may be formed substantially of the fabric under characterisation.

To enhance data collection and measurement accuracy, the volume of test liquid in said source reservoir may be substantially less than that in said container, and this will provide a smaller reference value for better measurement sensitivity.

To simulate the skin perspiration conditions of a human being, the apparatus may further comprise a temperature control arrangement for maintaining the test liquid in said container at a constant temperature.

According to the present invention, the respiratory or relevant properties of a fabric are characterised by tracking on the loss of test liquid through a fabric under characterisation, and through the monitoring of the amount of test liquid required to replenish the loss. More particularly, the loss of test liquid is monitored through tracking of test liquid loss from a source reservoir, while maintaining a constant test liquid mass in an intermediary test container constant, which supplies the test liquid to the fabric. The invention is advantageous since the weight (or mass) of the test liquid in the source reservoir can be only a fraction, say 10% to 50%) of the weight or mass of an entire structure carrying the test container and the test liquid, changes in mass in the source reservoir can be more easily and/or accurately detectable. Further, through the application of a testing methodology in which the test liquid delivery arrangement comprises the utilisation of a combination of a test container for carrying a test liquid of a constant mass and a source reservoir for carrying a variable mass of test liquid, different test containers or test container modules of various shape and configuration can be used to enhance the flexibility of the characterising method and/or apparatus.

BRIEF DESCRIPTION OF THE DRAWINGS

Preferred embodiments of the present invention will be described by way of example with reference to the accompanying drawings, wherein.

DETAILED DESCRIPTION OF THE PREFERRED EMBODIMENTS

Figure 1:
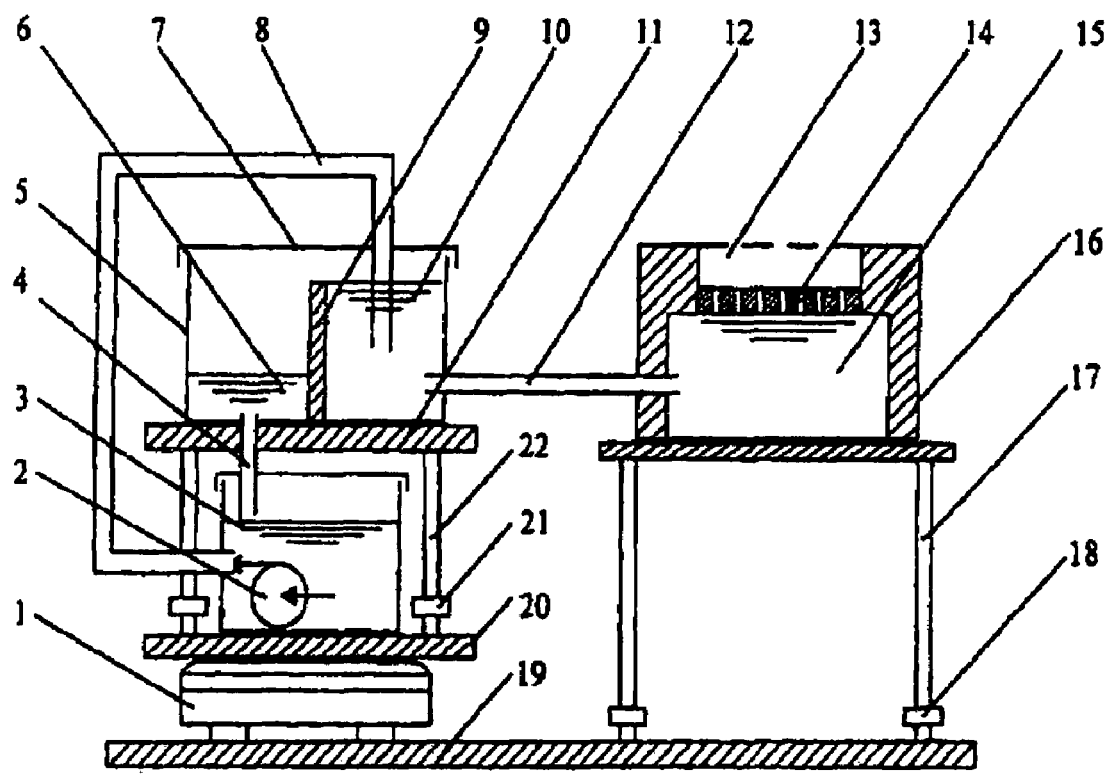
FIG. 1 is a schematic elevation of a fabric characterisation apparatus depicting a first embodiment of this invention.

In FIG. 1 of the accompanying drawings there is depicted schematically a fabric characterisation apparatus in the form of a tester for use in real-time measurement of water loss in water or moisture transport tests. The tester comprises a solid base 19 upon which there is located a load cell or electronic scale 1. Resting upon the load cell 1 is a covered lower water reservoir 3 having a pump 2 therein. Supported above the lower reservoir 3 by support posts 22 is a plate 11. The support posts 22 each comprise height adjustment knobs 21. A covered upper water reservoir 5 rests upon the plate 11. The upper reservoir 5 includes a weir 9 which divides the reservoir into a first (weir) section 10 and a second (overflow) section 6. A drainpipe 4 extends from the second section 6 to the lower reservoir 3. A flexible pipe 8 extends from the pump 2 in the lower reservoir to the first section 10 of the upper reservoir.

Also located upon the base 19 is a test block 16 on a plate that is supported by support posts 17, each having positioning knobs 18 therein. Within the test block 16, there is a test block water reservoir 15. A support member in the form of a perforated plate 14 covers the test block reservoir 15 and is in contact with the water therein. A sample chamber 13 is provided above the perforated plate 14 of the test block 16. The test block reservoir 15 is connected to the first section 10 of the upper reservoir 5 by a flexible pipe 12 through which water can migrate between the reservoirs.

Water stored in the lower reservoir 3 is pumped by pump 2 via pipe 8 to the first section 10 of the upper reservoir 5. The pump 2 is controlled so that the pumped water flow rate through the pipe 8 is sufficient to maintain a flow of water over the weir 9 from the first section 10 to the second section 6. Water from the second section 6 is returned to the lower reservoir 3 via the drainpipe 4. By turning knobs 21, the upper reservoir is adjusted vertically. As a consequence, the level of the upper edge of weir 9 is calibrated so that the constant water surface level of the continuously overflowing water in the first section 10 is maintained slightly higher than the level of the perforated plate 14 of the test block 16. This, in effect maintains a constant hydrostatic pressure resulting from a small head of water at the perforated plate 14. Moreover, the water level in the test block reservoir is not allowed to fall away from the perforated plate. Water from the test block reservoir 15 migrates upwardly through the perforated plate during testing.

Fabric samples are placed upon the perforated plate 14 in test chamber 13 of the test block 16. As water is absorbed by or transported through the fabric sample, water is replenished within the test block reservoir 15 by siphon action through the pipe 12 from the first section 10 of the upper reservoir. The water level within the test block reservoir 15 is thereby maintained constant. The rate of water absorbed or transported through the fabric can be accurately measured by recording readings from the load cell 1 over a test period and graphing these results.

In order to simulate real-life conditions, a temperature control arrangement (not shown) is provided to maintain the water at a relatively constant temperature, for example, at around 37.4 degrees celcius.

Test Results

Figure 2:
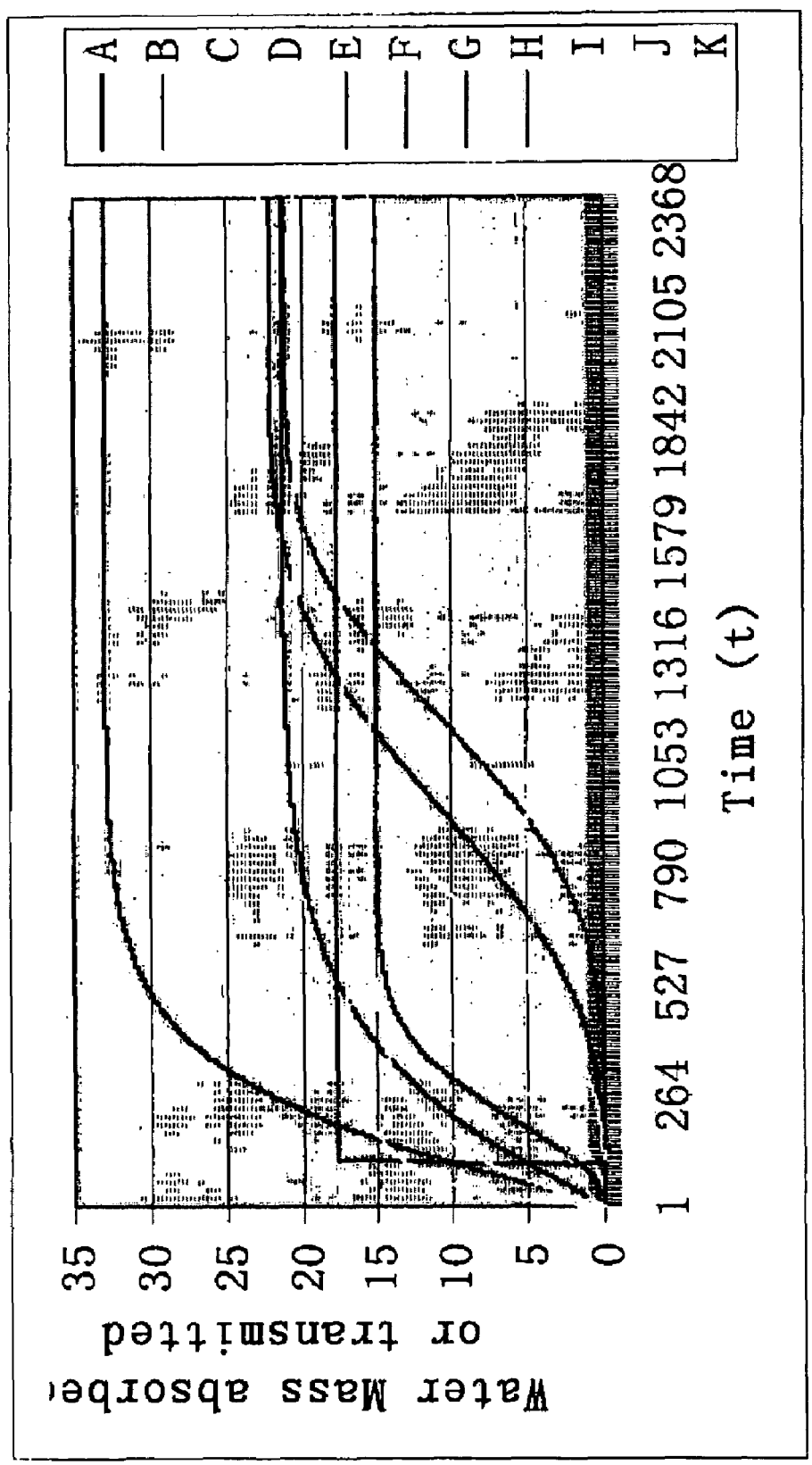
FIG. 2 is a graph showing water absorption or transmission vs. time for various test samples obtained using the apparatus of FIG. 1.

Experimental tests of the above-described tester have been carried out to determine the transplanar water transport properties of various fabric samples. The results are plotted in FIG. 2. The water absorption/transmission profiles as shown in FIG. 2 can be used to calculate various parameters. The initial water uptake of the fabric sample (the absorption of water in a specified initial few seconds) is defined by the slope of the curve at 50% saturation capacity and the rate of water transmission after saturation (the slope of the curve after 100% saturation) can readily be determined from the profiles.

It should be appreciated that modifications and alterations obvious to those skilled in the art are not to be considered as beyond the scope of the present invention. For example, either of height adjustment knobs 18 or 21 can be omitted as long as the height of perforated plate 14 can be adjusted relative to the water level in the first (weir) section 10. Furthermore, rather than providing manual height adjustment knobs, a water level sensor fixed in height relative to the perforated plate 14 might be provided at the first section 10 with electronic feedback control to an electro-mechanical height adjuster for the upper reservoir 5. Furthermore, the lower reservoir might be omitted and the pump might draw liquid directly from the overflow reservoir to the weir.

Figure 3:
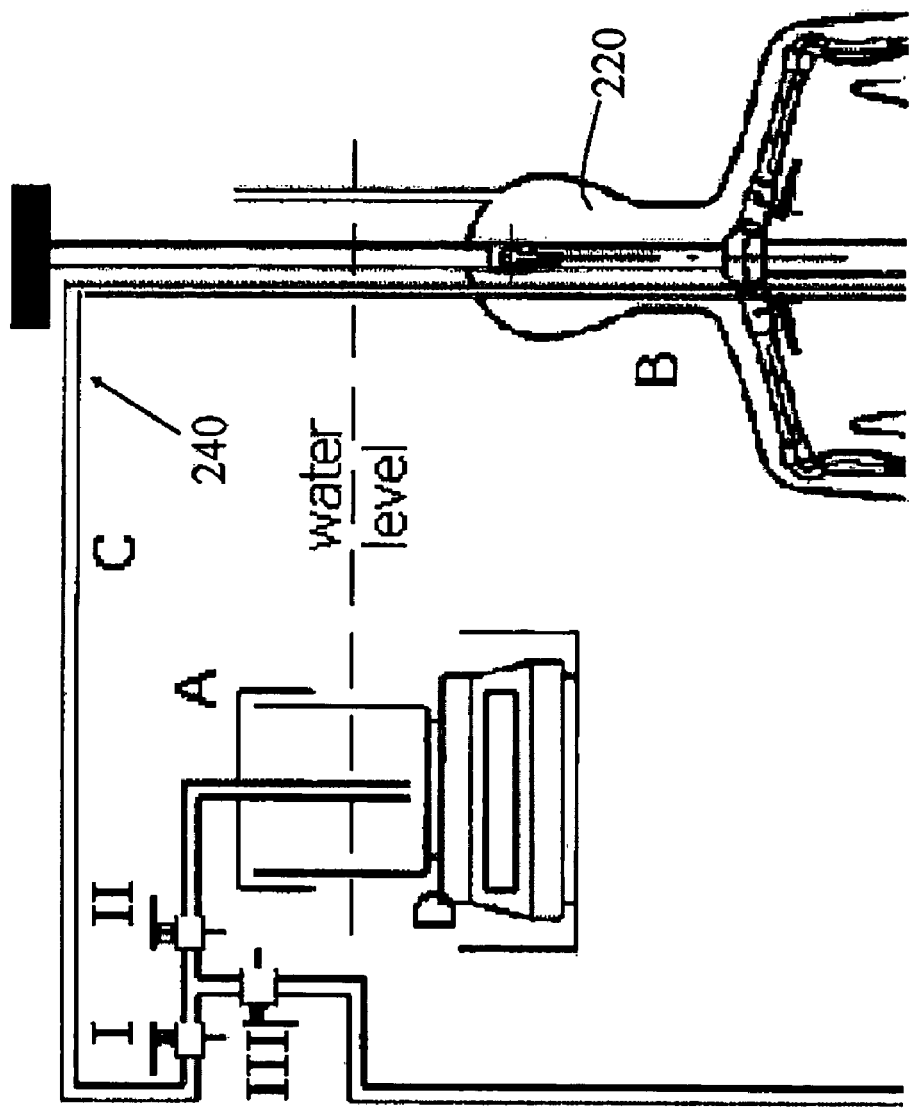
FIG. 3 is a schematic diagram depicting a second preferred embodiment of this invention.
Figure 4:
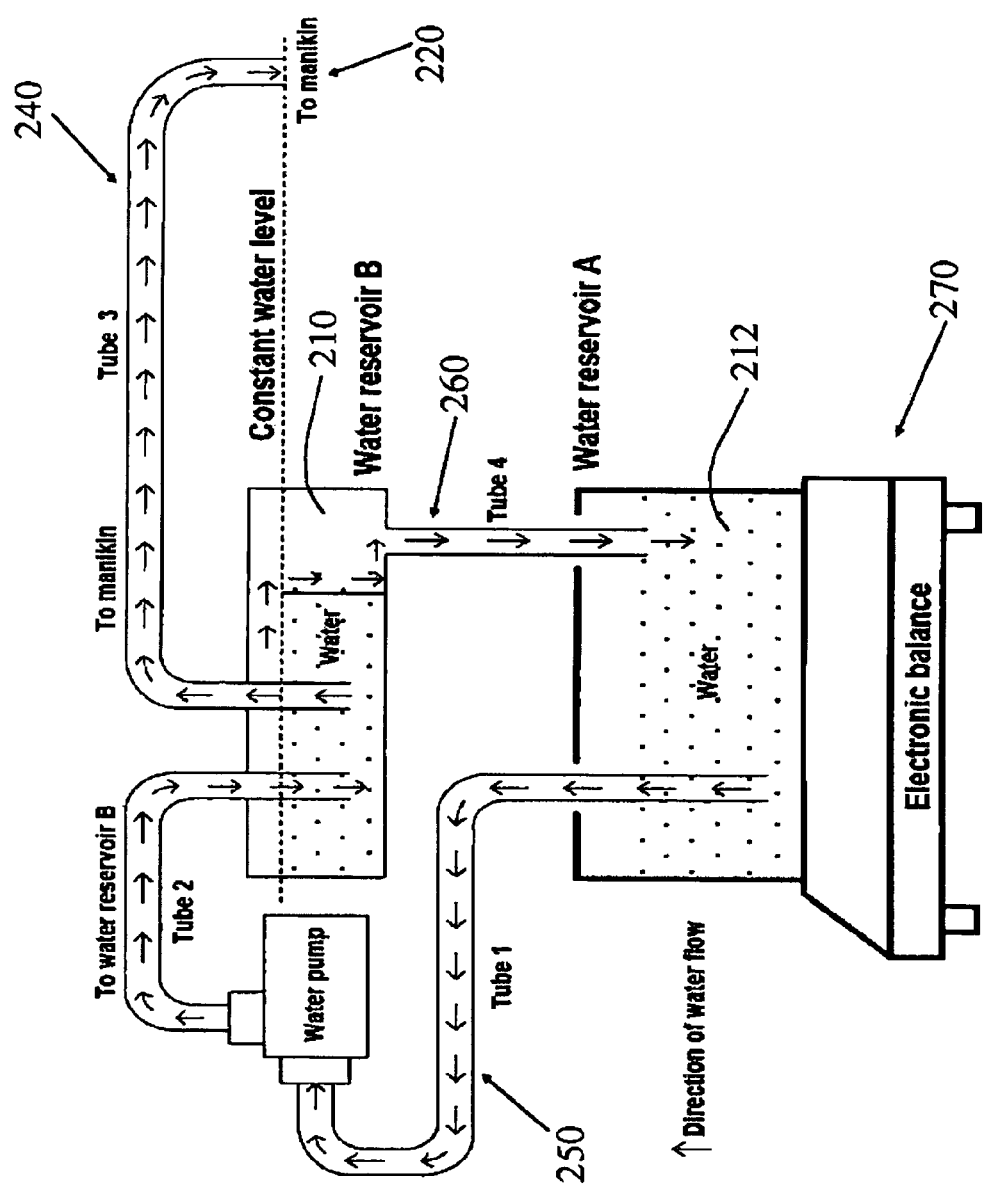
FIG. 4 shows in more detail a test liquid supply and monitoring system for use with the apparatus of FIG. 3.

In a second embodiment of this invention as depicted in FIGS. 3 and 4, the testing apparatus comprises a source reservoir 210 for supplying a test liquid 212 to a manikin 220, on which clothing may be put for testing its moisture transport properties. The test liquid is supplied from the source reservoir 210 to the manikin 220 via a first liquid delivery arrangement 240. As can be seen more clearly in FIG. 4, the source reservoir 210 comprises an overflow arrangement to maintain the level or volume of the test liquid in the reservoir, a liquid delivery arrangement 240 for replenishing test liquid to the manikin to compensate for loss of test liquid from the fabric enclosure due to moisture transmission there-through, and a second liquid delivery arrangement 250 for delivering the test liquid from the container 230 to the source reservoir 210. The overflow arrangement further comprises a liquid delivery arrangement 260 for returning the overflowed test liquid to the container 230. The container sits on an electronic scale 270 so that the volume of test liquid in the container can be monitored and the variation of test liquid can be accurately recorded.

As shown in FIG. 4, the apparatus is a substantially closed system and the test liquid is kept within the apparatus except for possible loss due to moisture transmission through the manikin 220. Thus, by maintaining the volume of the manikin at a constant volume, the loss of test liquid from the container 230 will be loss due to the fabric constructed manikin.

The manikin 220 is constructed substantially from a water proof, but moisture permeable fabric "skin" and is configured to resemble a human being in the a posture (e.g. standing, seated and lying down) for evaluating the moisture transport properties of the clothing put on the manikin. The fabric formed manikin 220 is configured to store a predetermined volume or level of test liquid and the actual test liquid volume or level is maintained by a level controlling arrangement connected to the source reservoir 210. When compared with the first embodiment of FIG. 1, the contact area between the test liquid and the fabric is substantially increased and useful data can be more conveniently collected. Some exemplary dimensions of the manikin (nicknamed 'Walter') are set out in Table 1 below.

TABLE 1

| Dimensions of Walter | |
|---|---|
| Height | 172 cm |
| Neck Circumference | 45 cm |
| Chest Circumference | 95 cm |
| Waist Circumference | 89 cm |
| Hip Circumference | 100 cm |
| Surface Area | 1.79 m2 |

In operation, the manikin 220 is filled with a test liquid, and the test liquid level in the manikin is maintained by hydrostatic pressure by means of a level control arrangement connected to the source reservoir. Since the liquid containing and delivery paths of the apparatus is closed and the only path of liquid loss is through the fabrics, the fabric moisture transmission characteristics can be determined by monitoring the loss of test liquid from the container 230. Moreover, because the volume or weight of the entire manikin when filled with the test liquid could be substantial, for example, at least 50% more than the volume of the source reservoir, a higher data sensitivity and/or accuracy could be obtained when an electronic scale of a resolution is used.

While the present invention has been explained by reference to the examples or preferred embodiments described above, it will be appreciated that those are examples to assist understanding of the present invention and are not meant to be restrictive. Variations or modifications which are obvious or trivial to persons skilled in the art, as well as improvements made thereon, should be considered as equivalents of this invention. For example, while a manikin is used as an example in the second embodiment described above, it will be appreciated that the arrangement can be adapted in the manner of the first embodiment with the manikin replaced by the container 15 and fabric receptacle 14 of FIG. 1.

Furthermore, while the present invention has been explained by reference to water as a test liquid, it should be appreciated that the invention can apply, whether with or without modification, to other test liquids, for example, saline, without loss of generality.

The invention claimed is:

1. A method of characterising liquid or moisture transmission properties of a fabric, the method comprising the steps of:
  filling a container with a test liquid,
  delivering said test liquid from said container towards said fabric for transmission of said test liquid from a testing apparatus externally of the apparatus through said fabric,
  supplying said test liquid from a source reservoir to said container to replenish liquid lost from said container due to transmission of moisture through said fabric, and
  measuring the amount of liquid loss from said source reservoir to determine the moisture transmission characteristics of said fabric,
  wherein the share of the container is reconfigurable to simulate a plurality of postures of a human being.

2. A method according to claim 1, wherein said container defines an aperture through which the test liquid contained in said container is transmissible outside of said container, and the method comprises covering said aperture with a fabric to be characterised.

3. A method according to claim 1, wherein the volume of said test liquid in said container is maintained constant by the replenishing liquid during the fabric characterisation process.

4. A method according to claim 1, wherein the level of said test liquid in said container relative to said fabric is maintained constant during the fabric characterisation process.

5. A method according to claim 1, wherein the liquid level in the source reservoir is maintained to be the same as the liquid level in said container by hydrostatic pressure.

6. A method according to claim 1, wherein the hydrostatic pressure of said test liquid in said container relative to said fabric is maintained constant during the fabric characterisation process.

7. A method according to claim 1, wherein the volume of test liquid contained in said source reservoir is smaller than the volume of test liquid in said container.

8. A method according to claim 1, wherein the volume of test liquid contained in said source reservoir is less than 50% of the volume of test liquid in said container.

9. A method according to claim 1, wherein the fabric and the test liquid in said container are arranged to simulate sweating conditions of a human being.

10. A method according to claim 1, wherein the fabric and the container are arranged so that loss of liquid from said container is solely due to transmission through said fabric.

11. A method according to claim 2, wherein the fabric forms at least part of said container and defines said aperture.

12. A fabric characterization apparatus for characterising the respiratory or moisture transmission properties of a fabric, the apparatus comprising:
   a container for receiving a test liquid and for supplying said test liquid to a fabric of which the moisture transmission properties are to be characterised,
   a source reservoir for supplying said test liquid to said container for replenishing said container with said test liquid to compensate for loss of said test liquid from said container, and
   a monitoring device for recording and monitoring the supply of the replenishing liquid from said source reservoir to said container,
   wherein the share of the container is reconfigurable to simulate a plurality of postures of a human being.

13. An apparatus according to claim 12, further comprising an arrangement for delivering the test liquid from said container to the fabric.

14. An apparatus according to claim 12, further comprising a receptacle for receiving said fabric, said receptacle defining an aperture through which said test liquid is transmissible outside of said container through said fabric.

15. An apparatus according to claim 12, further comprising a processor for compiling data taken by said monitoring device to evaluate breathing or respiratory properties of a fabric to be characterised.

16. An apparatus according to claim 12, wherein said source reservoir is sealed against loss of test liquid due to evaporation therefrom.

17. An apparatus according to claim 12, wherein said container comprises a receptacle defining an aperture and for receiving a fabric to be characterised, said receptacle and said aperture being arranged such that loss of test liquid from said container being solely through said aperture and said fabric.

18. An apparatus according to claim 17, wherein the level of said receptacle relative to said test liquid in said container is adjustable.

19. An apparatus according to claim 12, wherein said container comprises a liquid-permeable support member having a first surface for supporting a fabric test sample, and a second surface for interfacing with the test liquid in the source reservoir.

20. An apparatus according to claim 12, wherein said container comprises an overflow arrangement for maintaining a constant level or a constant volume of test liquid in said container, and said monitoring device is also arranged to monitor the overflow of said test liquid.

21. An apparatus according to claim 20, wherein the overflow level of said overflow arrangement is adjustable.

22. An apparatus according to claim 20, further comprising an overflow return arrangement for returning the overflowed test liquid to said source reservoir.

23. An apparatus according to claim 12, wherein the test liquid in said container is substantially surrounded by the fabric under characterisation.

24. An apparatus according to claim 23, wherein said container is formed substantially of the fabric under characterisation.

25. An apparatus according to claim 12, wherein the volume of test liquid in said source reservoir is substantially less that that in said container.

26. An apparatus according to claim 12, further comprising a temperature control arrangement for maintaining the test liquid in said container at a constant temperature.

* * * * *

UNITED STATES PATENT AND TRADEMARK OFFICE
CERTIFICATE OF CORRECTION

PATENT NO. : 7,730,775 B2  Page 1 of 1
APPLICATION NO. : 11/634077
DATED : June 8, 2010
INVENTOR(S) : Jintu Fan et al.

It is certified that error appears in the above-identified patent and that said Letters Patent is hereby corrected as shown below:

Col. 8,
Claim 1, line 15, replace "share" with --shape--.

Signed and Sealed this

Thirty-first Day of August, 2010

David J. Kappos
*Director of the United States Patent and Trademark Office*